United States Patent
Abou-Nemeh et al.

(10) Patent No.: US 6,348,264 B1
(45) Date of Patent: *Feb. 19, 2002

(54) PROCESS FOR PRODUCING LOW DE STARCH HYDROLYSATES BY NANOFILTRATION FRACTIONATION, PRODUCTS OBTAINED THEREBY, AND USE OF SUCH PRODUCTS

(75) Inventors: Ibrahim Abou-Nemeh, Quincy, IL (US); Michael A. Tripodi, Santa Fe, NM (US)

(73) Assignee: Roquette Freres, Lestrem (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/567,315

(22) Filed: May 9, 2000

Related U.S. Application Data (63) Continuation-in-part of application No. 09/221,902, filed on Dec. 28, 1998, now Pat. No. 6,068,705, which is a continuation-in-part of application No. 09/066,651, filed on Apr. 27, 1998, now Pat. No. 5,853,487.

(51) Int. Cl.$^7$ .............................................. C08B 31/00
(52) U.S. Cl. ...................... 428/402; 428/403; 428/407; 426/590; 426/661; 127/32; 127/71; 106/215.5
(58) Field of Search ................................ 428/402, 403, 428/407; 127/32, 71; 106/215.5; 426/590, 661

(56) References Cited

U.S. PATENT DOCUMENTS

| | | | |
|---|---|---|---|
| 3,756,853 A | 9/1973 | Meyer | 127/38 |
| 3,873,694 A | 3/1975 | Kanig | 424/648 |
| 3,974,032 A | 8/1976 | Harjes et al. | 426/661 |

(List continued on next page.)

FOREIGN PATENT DOCUMENTS

| | | |
|---|---|---|
| DD | 238 528 | 8/1986 |
| DD | 273 000 | 11/1989 |
| EP | 0 101 891 | 3/1984 |
| EP | 783300 | 7/1997 |
| EP | 0 853 578 | 11/1999 |
| WO | 93 25078 | 12/1993 |
| WO | WO97/48392 | 12/1997 |
| WO | 98 05688 | 2/1998 |
| WO | WO99/08659 | 2/1999 |
| WO | WO99/09959 | 3/1999 |

OTHER PUBLICATIONS

Kearsley, et al., << Reverse Osmosis of Glucose Syrups >>, Die Starke Jan. 28, 1976, Nr.4, pp. 138–144.

Birch, et al., << The Fractionation of Glucose Syrups by Reverse Osmosis >>, Apr. 22–26, 1974, pp. 2240–224.

R. J. Peterson, et al., << Thin Film Composite Reverse Osmosis Membranes >> Handbook Industrial Membrane Technology, pp. 321–327.

(List continued on next page.)

Primary Examiner—Leszek Kiliman
(74) Attorney, Agent, or Firm—Henderson & Sturm LLP

(57) ABSTRACT

A process for producing solid forms comprising the steps of: (1) forming an aqueous composition comprising the low DE starch hydrolysate of the invention; (2) drying said aqueous composition to result in a substantially dry low DE starch hydrolysate composition; (3) shaping said dry low DE starch hydrolysate composition to result in a solid form.

A process for producing a coated solid form, comprising the steps of forming an aqueous composition comprising the low DE starch hydrolysate of the present invention and applying to the solid form said aqueous composition in order to form a coated solid form.

A process for producing a substantially dry granular low DE starch hydrolysate composition comprising the steps of: (1) forming an aqueous composition comprising the low DE starch hydrolysate of the present invention; (2) drying said aqueous composition to result in a substantially dry low DE starch hydrolysate composition; (3) granulating the low DE starch hydrolysate composition to result in a granular substantially dry low DE starch hydrolysate product.

29 Claims, 1 Drawing Sheet

U.S. PATENT DOCUMENTS

| | | | | |
|---|---|---|---|---|
| 3,974,033 A | | 8/1976 | Harjes et al. | 435/99 |
| 3,974,034 A | | 8/1976 | Horn et al. | 435/99 |
| 4,298,400 A | | 11/1981 | Ambruster | 127/29 |
| RE30,880 E | | 3/1982 | Armsbruster | 435/99 |
| 4,439,453 A | | 3/1984 | Vogel | 514/629 |
| 4,551,177 A | | 11/1985 | Trubiano et al. | 106/206.1 |
| 4,840,807 A | | 6/1989 | Yoshida et al. | 426/48 |
| 5,057,321 A | | 10/1991 | Edgren et al. | 424/473 |
| 5,612,202 A | | 3/1997 | Brumm | 435/99 |
| 5,853,487 A | * | 12/1998 | Tong | 127/32 |
| 6,010,719 A | | 1/2000 | Remon et al. | 424/464 |
| 6,068,705 A | * | 5/2000 | Tong | 127/32 |

OTHER PUBLICATIONS

L. P. Raman, << Consider Nanofiltration for Membrane Separations >>, Chemical Engineering Progress, Mar. 1994, pp. 68–74.

R. D. Waniska, et al., << Comparison of Methods for Separating Oligosaccharides : Unifiltration >>, Journal of Food Science, vol. 45, 1980, pp. 1260–1284.

H. R. Sloan, et al., << Large Scale Production of Glucose Oligomers and Polymers for Physiological Studies in Humans >>, Preparative Biochemistry, 1954(4), (1985), pp. 259–279.

European Search Report, Aug. 21, 2001, The Hague.

* cited by examiner

PROCESS FOR PRODUCING LOW DE STARCH HYDROLYSATES BY NANOFILTRATION FRACTIONATION, PRODUCTS OBTAINED THEREBY, AND USE OF SUCH PRODUCTS

CROSS-REFERENCE TO RELATED APPLICATIONS

This application is a Continuation-in-part of U.S. Application Ser. No. 09/221,902, filed Dec. 28, 1998, entitled "Process for Producing Low DE Starch Hydrolysates By Nanofiltration Fractionation, Products Obtained Thereby, and Use of Such Products," now U.S. Pat. No. 6,068,705, which is in turn, a Continuation-in-part of U.S. Application Ser. No. 09/066,651, filed Apr. 27, 1998, entitled "Process for Producing Low Starch Hydrolysates By Nanofiltration Fractionation and Blending of Resultant Products, Preferably in Liquid Form, With Other Carbohydrates," now U.S. Pat. No. 5,853,487, both disclosures of which are hereby incorporated by reference in its entirety.

BACKGROUND OF THE INVENTION

1. Field of the Invention

The present invention is directed to producing low DE starch hydrolysates, which involves fractionating a starch hydrolysate having a DE greater than about 18 using a nanofiltration membrane under nanofiltration conditions effective to result in low DE starch hydrolysate having a DE of less than about 25; resultant low DE starch hydrolysate products; blends of such low DE starch hydrolysates with other substances; use of low DE starch hydrolysate products having a DE of less than about 25 and a polydispersity of less than about 5 as a binder and/or filler for solid and liquid delivery systems; producing an enlarged, dust-free, flowable granulated powder from such low DE starch hydrolysates; use of such low DE starch hydrolysates in coating solid forms.

2. Description of the Related Art

Maltodextrins, a low DE starch hydrolysate with a dextrose equivalent (DE) of not more than about 20, e.g., 4 to 20, have bland taste, low sweetness, and low hygroscopicity. Such products are useful as bases for the preparation of food items as well as for bodying agents and as additives having non-sweet, water-holding, non-hygroscopic characteristics. Other applications include their use as a carrier for synthetic sweeteners, as spray drying adjunct, as bulking, bodying or dispersing agents, as moisture holding agents, and as energy source in sports drinks.

Most commercially available maltodextrins in the world market produced by known technology are in the solid form or crystalline form due to retrogradation or haze formation or microbial instability in liquid form. However, there is a demand for a maltodextrin in its liquid form, which exhibits extreme clarity, low viscosity, and will not develop retrogradation upon storage at room temperature.

There has been low DE liquid maltodextrins produced using conventional processes, such as enzyme conversion, chromatographic fractionation and membrane fractionation. However, the products produced suffered disadvantages including instability in liquid form or high viscosity.

U.S. Pat. Nos. 3,974,033 and 3,974,034 disclose methods to produce a low DE maltodextrin and improve stability by enzymatic hydrolysis of oxidized starch. The maltodextrin is characterized as being haze-free for long period of time at high solids concentration. The maltodextrin is prepared by first liquefying a highly oxidized starch with acid or enzyme to a DE not substantially above about 7; and, in a subsequent step, converting the oxidized and liquefied starch with a bacterial alpha-amylase enzyme preparation to achieve a maltodextrin product having a DE not substantially above about 20.

U.S. Pat. No. 4,298,400 discloses another enzyme hydrolysis method to produce non-haze low DE liquid starch hydrolysates. The product, prepared by two step hydrolysis both using bacterial alpha amylase, has a descriptive ratio higher than 2.0, and, therefore, exhibits non-haze property.

U.S. Pat. No. 4,840,807 discloses a fractionation method to produce liquid low DE branched maltodextrins. The process comprises the steps of reacting alpha-amylase with starch to produce a starch hydrolysate in the DE range of 10 to 35, and then contacting the resulting saccharified solution with a gel-type filter agent, thereby selectively fractionating the branched dextrin and linear oligo-saccharides. The gel-type filtering agent is an ion exchange resin and the fractionation system is a simulated moving bed. The resulted branched oligosaccharides has a mean molecular weight of from about 800 and to about 16,000 with a corresponding DE from about 20 to about 1.

Membrane separation is known to fractionate polysaccharides of sugars. Waniska et al. (Journal of Food Science, Vol. 45 (1980), 1259) discloses the fractionating ability of three ultra filtration (UF) membranes compared with gel permeation and chromatography for separating oligosaccharides (DP5–20) from lower molecular sugar. Birch et al. (Die Starke 26. Jahrg. 1974/Nr.7, 220) discloses the fractionation of glucose syrups by reverse osmosis (RO) which offers a means for the manufacture of several new types of syrup, and which enables entire groups of sugars to be eliminated under selected conditions. Products in the range 43–80 DE or 15–43 DE can be obtained using suitable combinations of different membranes. Kearsley et al. (Die Starke 28. Jahrg. 1976/Nr. 4, 138) discloses the reverse osmosis(RO) of glucose syrups and ultra filtration (UF) operations to isolate specific groups of sugars, high or low molecular weight or both, from the syrup. Sloan et al. (Preparative Biochemistry, 15(4), 1985, 259–279) discloses the molecular filtration of ultra filtration (UF) membranes to concentrate oligosaccharides with degrees of polymerization above 10 from corn starch hydrolysate. It is not believed that any of these processes has been used to make a non-retrograded maltodextrin having low viscosity.

Those concerned with low DE starch hydrolysates recognize the need for an improved low DE starch hydrolysate, particularly in liquid form, and more particularly, in blends thereof with other substances.

It is well known that in order to form an acceptable tablet a binder and/or filler must have several attributes. Ideally, a binder or filler would possess the following properties: (1) inertness, non-reactiveness; (2) high degree of plastic deformation; (3) low elastic modulus; (4) high dislocation density; (5) tasteless and odorless; (6) non-hygroscopic or slightly hygroscopic; (7) chemically and physically compatible with other ingredients such as lubricants, flow and disintegration aids, colorants, dyes; (8) fast disintegration if desired ; (9) no bioavailability hindrance or delay; (10) aging stability; and/or (11) a high loading/carrying capacity for active ingredients. Those principles arc described in U.S. patent applications Ser. No.: 4,551,177; 5,057,321, 3,873, 694, 4,439,453; in WO 99/09959, WO 97/48392; EP 0783300; WO 99/08659.

Currently, there are many available binders and fillers including vehicles such as spray-dried lactose, pregelatinized starch, microcrystalline cellulose (MCC), sorbitol, hydroxypropylmethyl cellulose (HPMC). However, many binders and fillers have well known disadvantages. For example, lactose is known to discolor upon contact with amines, phosphates, lactates, or moisture. MCC requires a dry storage atmosphere for fluffiness and to obtain good tabletting results. Starches often lead to discoloration and high viscosity. HPMC and other cellulosics can impart a slimy taste, Taxation effects, high foam and increased color. Accordingly, those concerned with the art of formulating delivery systems recognize the need for binders and fillers with improved functionality, and stability upon aging.

BRIEF SUMMARY OF THE INVENTION

The present invention is directed to a process for producing a low DE starch hydrolysate, which involves fractionating a starch hydrolysate having a DE greater than about 18 using a nanofiltration membrane, preferably selected from the group consisting of Teflon membranes, stainless steel membranes, ceramic membranes, and polymeric membranes; and/or having a molecular weight cut-off of less than about 4,000 daltons, under nanofiltration conditions effective to result in low DE starch hydrolysate having a DE of less than about 25.

In accordance with the present invention, such nanofiltration membranes preferably comprise a thin film composite membrane, wherein the preferred thin film composite membrane is selected from the group consisting of polyamide membranes and polysulfonated polysulfone membranes.

In one embodiment of the present invention, the low DE starch hydrolysate comprises a liquid, low DE starch hydrolysate having a DE of less than about 25 and a polydispersity index of less than about 5. The liquid, low DE starch hydrolysate preferably comprises a dry solids content within a range of about 50% to about 85%, and/or a viscosity at 70% dry solids content and at 25° C. of less than about 30,000 centipoise. The liquid low DE starch hydrolysate preferably is substantially non-retrograding and microbial stable.

The present invention also involves hydrogenating, and/or derivatizing, and/or drying the low DE starch hydrolysate of the present invention to result in an hydrogenated, and/or derivatized, and/or dry low DE starch hydrolysate.

It is accordingly an objective of the present invention to provide a nanofiltration membrane process for producing low DE starch hydrolysates having a DE less than about 25 and a polydispersibility index of less than about 5, particularly in their liquid form which are eventually substantially retrogradation free, and have lower viscosity at high dry solids compared to conventional products.

The liquid form and its characteristics of low viscosity are particularly suitable for drying, preferably by spray drying or extrusion, the liquid to result in a solid or substantially dry product.

The present invention is also directed to a process for producing solid forms comprising the steps of forming an aqueous composition comprising at least one member selected from the group consisting of low DE starch hydrolysate of the present invention, in its non-hydrogenated, or hydrogenated, or derivatized form; drying said aqueous composition to a moisture content of less than about 10% to result in a substantially dry low DE starch hydrolysate composition; and shaping said dry low DE starch hydrolysate composition to result in a solid form.

In one embodiment of the present invention, the process for producing solid forms further comprises a step of granulating (during and/or after the drying step) the substantially dry low DE starch hydrolysate composition to result in a granular substantially dry low DE starch hydrolysate composition. As used herein, granulating refers to the process of particle size enlargement and may be accomplished by granulation, agglomeration, compaction, or other suitable means.

In another embodiment of the present invention, the aqueous composition further comprises an effective concentration of at least one other ingredient.

It is yet another objective of the present invention to provide a process for producing a coated solid form, comprising the steps of: forming an aqueous composition comprising at least one member selected from the group consisting of low DE starch hydrolysate of the present invention in its non-hydrogenated, or hydrogenated, or derivatized form; and applying to the solid form said aqueous composition in order to form a coated solid form.

In one embodiment of the present invention, the aqueous composition further comprises an effective concentration of at least one ingredient selected from the group consisting of sugars; sugar alcohols; cellulosic polymers such as microcrystalline cellulose, hydroxypropylmethyl cellulose, hydroxyethyl cellulose; polymeric ingredients such as polyvinyl pirrolydone (PVP) of varied molecular weight from 20,000 to 2,000,000; starches (modified and/or pregelatinized), protein based ingredients such as gelatine and pectin, preservatives, flavours, colourings.

It is yet another objective of the present invention to provide a process for producing a substantially dry granular low DE starch hydrolysate composition comprising the steps of: forming an aqueous composition comprising at least one member selected from the group consisting of low DE starch hydrolysate, in its non-hydrogenated, or hydrogenated, or derivatized form; drying said aqueous composition to a moisture content of less than about 10% to result in a substantially dry low DE starch hydrolysate composition; and granulating the low DE starch hydrolysate composition to result in a granular substantially dry low DE starch hydrolysate product.

DETAILED DESCRIPTION OF THE INVENTION

Figure 1:
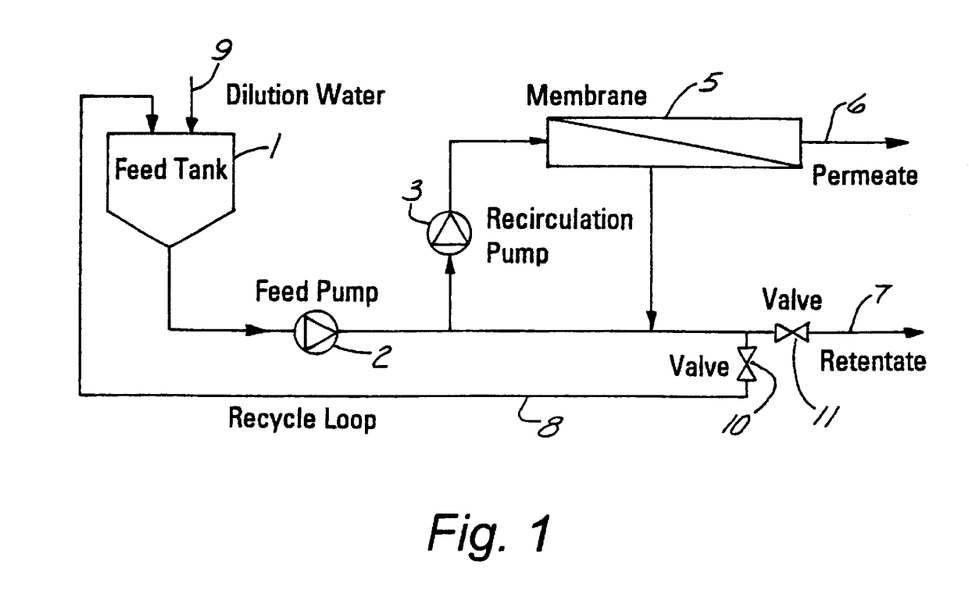
The FIGURE shows a flow diagram for a nanofiltration process in accordance with the present invention.

The following is a detailed description of the present invention intended to be claimed:

The low DE starch hydrolysates of the present invention are produced by a nanomembrane filtration process shown in FIG. 1.

In general, the process for producing a low DE starch hydrolysate in accordance with the present invention involves fractionating a starch hydrolysate having a DE greater than about 18, and in particular greater than about 21, using a nanofiltration membrane, preferably selected from the group consisting of Teflon membranes, stainless steel membranes, ceramic membranes, and polymeric membranes, and/or having a molecular weight cut-off of less than about 4,000 daltons, under nanofiltration conditions effective to result in low DE starch hydrolysate having a DE of less than about 25.

The starch hydrolysate having a DE greater than about 18 suitable for purposes of the present invention are starch hydrolysates having a DE greater than about 18, and in particular greater than about 21, and which may be in non-hydrogenated, hydrogenated, oxidized or other derivatized form, which are effective in resulting in a low DE starch hydrolysate having a DE of less than about 25 upon fractionation in accordance with the present invention.

In accordance with the present invention, the polymeric nanofiltration membranes are preferably selected from the group consisting of polyamide membranes and polysulfonated polysulfone membranes.

For purposes of the present invention, the nanofiltration membranes are more preferably selected from the group consisting of polyamide membranes and polysulfonated polysulfone membranes having a molecular weight cut-off within a range of about 400 to about 4,000 daltons, more preferably within a range of about 800 daltons to about 2,500, and most preferably of about 1,000 daltons. Such nanofiltration membranes preferably comprise a thin film composite membrane, wherein a preferred thin film composite membrane is selected from the group consisting of polyamide membranes and polysulfonated polysulfone membranes. Specific examples of nanofiltration membranes include membranes selected from the group consisting of ASP40 and ASP50 (manufactured by Advanced Membrane Technology); and GH and GE, (manufactured by Osmonics/Desal). The thin film composite membranes may comprise polysulfone as support and polyester as backing. The membrane configuration may be selected from the group consisting of flat sheets, tubes, and spiral wound membranes.

The flux of permeate, defined as gallons per square foot per day, in nanofiltration processes in accordance with the present invention varies with pressure. The higher the pressure, the higher the flux. In accordance with the process of the present invention, the nanofiltration step of the present invention is operated at a pressure preferably of less than about 600 psi, and most preferably within a range of about 100 psi and about 500 psi. In contrast, conventional reverse osmosis processes typically require 500 to 2,500 psi operating pressure in order to obtain meaningful flux. In accordance with the present invention, for a permeate flux of a starting material feed of corn syrup having a DE 36 and a 30% dry solids at 50° C. and a pressure of about 480 psi is not less than 12 gallon per square foot per day (GFD).

The permeate flux in nanofiltration process also varies with different temperature. An increase of the operating temperature of about 10° C. can increase the flux by as much as 100%. However, as the operating temperature is increased, there is an increase in the tendency of certain membranes (e.g., polymeric) to rupture. As a result, the nanofiltration step of the processes of the present invention is operated at as high a temperature as possible to obtain maximum permeate flux without damaging membrane materials and structure or degrading the product. Accordingly, the operating temperature of the nanofiltration processes of the present invention is preferably less than about 95° C., more preferably within the range of about 40° C. to about 80° C., and most preferably at about 45° C. to about 65° C.

Accordingly, a low DE starch hydrolysate is fractionated using such a nanofiltration membrane under nanofiltration conditions which comprise a pressure less than about 600 pounds per square inch, preferably wherein the pressure is less than about 500 psi; and a temperature less than about 95° C., preferably wherein the temperature is less than about 80° C.

The nanofiltration step of the present invention can be operated as a batch operation or continuous operation. A batch operation can be operated using a closed single nanofiltration membrane element or a plurality of nanofiltration membrane elements in parallel or series, wherein a given starch hydrolysate as starting material feed is fractionated through a suitable nanofiltration membrane at a pressure and a temperature within previously described pressure ranges and temperature ranges, respectively, with retentate being recycled back to the feed tank to reduce the DE of the material in the feed tank and thus obtain a low DE starch hydrolysate having the desired DE value. In continuous operation, the starch hydrolysate as a starting material feed can be pumped through a series of membrane elements in serial or serial-parallel set-up for fractionation to reduce the DE of the starch hydrolysate and obtain a low DE starch hydrolysate having the desired DE value.

In one embodiment, the process of the present invention comprises refining the starch hydrolysate having a DE greater than about 18. Then, said starch hydrolysate is refined prior to fractionation using nanofiltration membrane. The refining step takes place before membrane separation.

In another embodiment, the process of the present invention comprises refining the low DE starch hydrolysate. The refining step takes place after membrane separation. Obviously, it is possible to have refining steps both before and after the membrane separation step.

For purposes of the present invention, refining comprises more preferably a conventional carbon treatment and a conventional ion exchange treatment of the material to be refined to de-color and de-ash the material.

Referring to FIG. 1, at the beginning of the process, starting material, i.e., corn syrup at about 30% dry substance, is transferred into the feed tank (1). The corn syrup starting material preferably has a DE greater than about 18 DE. The starting material as a feed is pumped through a feed pump (2) to a membrane element. A recirculation pump (3) is used to increase cross flow velocity of the liquid. The feed material is subjected to membrane fractionation by permeation of small molecular weight materials such as oligosaccharides lower than DP5 through a nanofiltration membrane, which retains large molecular weight materials. Permeate (6) from the membrane (5) is taken out of the system. The retentate (7) from the membranes (5) is recycled (8) back to the feed tank (1) until the DE of the retentate (7) reaches target, preferably lower than 20 DE. Since retentate (7) is recycled (8) to the feed tank (1) during batch processing, the dry substance increases. Therefore, dilution water (9) needs to be added in order to maintain high flux of membrane fractionation. In continuous processing, valve (10) is always closed, and there is no recycle fluid back to the tank.

In one embodiment of the present invention, the low DE starch hydrolysate, which is produced, comprises a liquid, low DE starch hydrolysate having a DE of less than about 25. The liquid, low DE starch hydrolysate preferably comprises a dry solids content within a range of about 50% to about 85%. The liquid, low DE starch hydrolysate preferably has a viscosity at 70% dry solids content and at 25° C. of less than about 30,000 centipoise (cp), measured using a Brookfield viscometer. For purposes of the present invention, the viscosity at 70% dry solids by weight and at 25° C. is more preferably between about 4,000 cp and 20,000 cp.

The low DE starch hydrolysates produced in accordance with the present invention have lower viscosity than conventionally acid or enzyme converted material having substantially the same DE. For the same DE product, viscosity increases with a higher concentration of long chain molecular (e.g., oligosaccharides of DP21+). Although not wishing to be bound by any particular theory, the lower viscosity property of products produced in accordance with the present invention is attributed to its lower weight concentration of DP21+which was only about 11 % at about 14 DE. This is in contrast to conventionally converted 14 DE maltodextrin which has at least about 40% DP21+. In general, a nanofiltration membrane produced maltodextrin of 18 DE and 70% dry substance at 25° C. has a viscosity of less than about 8,000 centipoise. While the conventionally enzyme converted maltodextrin of the same DE, same dry substance and at the same temperature has a viscosity of about 20,000 centipoise (cp). The low viscosity of the low DE starch hydrolysates and maltodextrins produced in accordance with the present invention allows such products to be concentrated or evaporated up to about 80% dry solids content, or higher, without any handling difficulty.

A high content of dry substance, e.g., equal or above about 75%, results in an additional advantage of the low DE starch hydrolysates of the present invention which is microbial stability. Water activity of low DE starch hydrolysates and maltodextrins produced in accordance with the present invention at a dry solids content of about 75% weight concentration is lower than about 0.86 at room temperature, which is stable enough for shipping in liquid form.

The low DE starch hydrolysate product of the present invention preferably has a DE of less than about 25, a polydispersity index of less than about 5, less than about 10% weight concentration of mono- and di- saccharides, and less than about 40% weight concentration of oligosaccharides with degree of polymerization higher than about 21. Preferably the low DE starch hydrolysate product comprises liquid, low DE starch hydrolysate having a moisture content within a range of about 50% to about 85% and/or a viscosity at 70% dry solids content and at 25° C. of less than about 30,000 cp, preferably wherein the viscosity is within the range of about 2,000 cp to about 25,000 cp, and more preferably about 4,000 cp to about 20,000 cp.

In accordance with the present invention preferred low DE starch hydrolysate products have a DE within a range of about 4 up to about 20; the concentration of mono- and di-saccharides is less than about 10% by weight; and the concentration of oligosaccharides having a degree of polymerization higher than about 21 is less than about 35%, and preferably less than about 30% by weight.

Low DE starch hydrolysates produced in accordance with the present invention exhibit liquid solution stability, low viscosity, and may remain substantially retrogradation free over extended periods of time, even at high dry solids content, at refrigeration and room temperatures. The low DE starch hydrolysates and maltodextrins of the present invention normally have a DE not substantially above 25 for low DE starch hydrolysates and not substantially above 20 for maltodextrins. The low DE starch hydrolysates and maltodextrins of the present invention preferably have a DE within the range of 4 to 20. A typical maltodextrin produced in accordance with the present invention generally has a DE within the range of about 8 to about 18.

As used herein, low DE starch hydrolysate means a starch hydrolysate having a DE of not greater than about 25. Maltodextrin is a starch hydrolysate having a DE of not greater than about 20.

The term "dextrose equivalent (DE), referred to herein, is defined as the reducing value of the maltodextrin or starch hydrolysate, material compared to the reducing value of an equal weight of dextrose, expressed as percent, dry basis, as measured by the School method described in Encyclopedia of Industrial Chemical Analysis, Vol. 11, pp. 41–42.

The term "polydispersity index", also referred to as "polymolecularity index", is defined as the ratio Mw/Mn, wherein Mw is the weight-average molecular weight and Mn is the number-average molecular weight. This ratio enables the overall dispersity of the molecular weights of a polymeric mixture to be characterized. In practice, the values of Mw and Mn may be determined by gel permeation chromatography, which is a technique well known by those skilled in the art.

The terms "non-retrograding", "retrogradation free", and the like are intended to be synonymous with "non-hazing" which is defined as having less than about 0.3 absorbency, and preferably less than about 0.1 absorbency, measured spectrophotometrically at about 600 nm, after storage at room temperature, i.e., about 23° C., for about three (3) months.

As used herein, the terms "stable", "stability", and the like refer to microbial stability and/or physical stability.

Although the present invention is disclosed using corn starch hydrolysates, also referred to as "corn syrup", derived from standard amylose-content corn as starting materials, glucose syrups and other starch hydrolysates from various cereal (e.g. wheat), tuber (e.g. potato), or other (e.g. chicory) starch sources and types (e.g. waxy) may be used.

The low DE starch hydrolysates of the present invention have a narrow saccharide distribution. In general, the polydispersity index is less than about 5 and the amount of monosaccharides and disaccharides is less than about 10% by weight and the amount of oligosaccharides of polymerization higher than about 21 is less than about 40% by weight, preferably less than about 35% by weight, and more preferably less than about 30% by weight.

The low DE starch hydrolysate may be used in producing a blend comprises liquid, low DE starch hydrolysate which is substantially non-retrograding, with at least one other substance in a predetermined blending ratio to result in a low DE starch hydrolysate-blend.

The other substance is preferably a carbohydrate selected from the group consisting of sugar alcohols like sorbitol, mannitol, xylitol, maltitol, erythritol, isomalt, and hydrogenated starch hydrolysates (e.g. maltitol syrups), propylene glycol, glycerine, and saccharides like inulin, glucose syrup, maltose syrup, and fructose syrup, lactose, erythrose, xylose and isomaltose. Preferably the low DE starch hydrolysate-blend produced in accordance with this embodiment of the present invention is substantially non-retrograding.

The low DE starch hydrolysates and maltodextrins produced by the nanofiltration membrane fractionation process of the present invention can be mixed, blended or otherwise combined with such substances to obtain a blended product having a lower viscosity and water activity than a blended product using conventional maltodextrins of substantially the same DE.

The process of the present invention also involves drying the liquid, low DE starch hydrolysate to result in a substantially dry product. Preferably the resulting low DE starch hydrolysate has a moisture content of less than about 10% by weight.

Drying means which may be used for purposes of dehydrating the liquid low DE starch hydrolysate in accordance with the present invention include conventional dehydration apparatus and methods suitable for dehydrating liquids having characteristics, such as viscosity, similar to those of the low DE starch hydrolysates. Preferably the drying comprises spray drying or extrusion.

The process of the present invention also involves hydrogenating the low DE starch hydrolysate having a DE of less than about 25 to result in a hydrogenated low DE starch hydrolysate, preferably wherein the hydrogenated low DE starch hydrolysate comprises liquid hydrogenated low DE starch hydrolysate or wherein the hydrogenated low DE starch hydrolysate comprises substantially dry hydrogenated low DE starch hydrolysate.

A co-hydrogenation of a low DE starch hydrolysate-blend may be also directed. Preferably, this co-hydrogenation comprises blending a low DE starch hydrolysate produced by nanofiltration in accordance with at least cast one other substance, preferably a carbohydrate as defined hereabove, to form a low DE starch hydrolysate-blend; and hydrogenating the low DE starch hydrolysate-blend to result in an hydrogenated low DE starch hydrolysate-blend.

To obtain the corresponding hydrogenated products, i.e., hydrogenated low DE starch hydrolysates and blends described above, they may be subjected to conventional hydrogenation. For example, the low DE starch hydrolysate resulting from nanofiltration fractionation may be subjected to the Raney nickel method of hydrogenation under suitable conditions therefor.

Thus, in accordance with the present invention, low DE starch hydrolysate and maltodextrin products may be liquid or substantially dry, hydrogenated or non-hydrogenated, substantially non-retrograding or retrograding, and blended with a carbohydrate or other substances or not. The hydrogenated form of the low DE starch hydrolysate and maltodextrin, may be obtained by conventional hydrogenation of the low DE starch hydrolysate, through hydrogenation of the starch hydrolysate starting material, or by co-hydrogenation of a blend comprising low DE starch hydrolysate and other substances, which may be carbohydrates.

Referring now to FIG. 1, in accordance with the process of the present invention, a conventionally converted corn starch hydrolysate, also referred to herein as "syrup" and "corn syrup", with a DE greater than about 18 DE, and preferably greater than about 21 DE, and in particular within a range of about 28 DE to 50 DE, is fed into a nanofiltration membrane, as shown in FIG. 1, for fractionation. The permeate from the membrane is taken out of the system, and the retentate is recycled to the feed tank for further concentration. Once the DE value of retentate reaches a target level, which is less than about 25 DE, preferably within a range of about 8 to about 20 DE, valve (11) in FIG. 1 is opened and valve (10) is closed. The retentate is sent forward into a storage tank as product. Operating pressures and temperatures are important process parameters. For purposes of the present invention, the operating pressure of the system is controlled to below about 600 psi, and preferably below about 500 psi. For purposes of the present invention, the operating temperature of the system is controlled to below about 95° C., and more preferably below about 80° C. For purposes of the present invention, a pH between about 2 to about 10 is preferred; and a pH between about 3 to about 8 is more preferred.

More specifically, in the process of the present invention, an acid converted starting material, such as corn starch hydrolysates (syrup) with a DE within a range of about 25 DE to about 63 DE, but preferably within a preferred range of about 25 DE to about 42 DE, is pumped through a nanofiltration membrane for fractionation at a trans-membrane pressure less than about 500 psi, permeate is removed from of the system and retentate is recycled to the feed until the DE of the syrup has been reduced to a desired level which is less than about 25 DE, and preferably within a range of about 8 to about 20.

For purposes of the present invention, the DE of the starch hydrolysate starting material is not less than about 18 DE, preferably not less than about 21 DE, more preferably within a range of about 25 to about 63 DE, and most preferably is within the range of about 25 to about 42 DE.

For purposes of the present invention, the preferred starch hydrolysate comprises a member selected from the group consisting of corn starch hydrolysate, wheat starch hydrolysate, root starch hydrolysate, and waxy maize starch hydrolysate, and the like most preferably wherein the starch hydrolysate comprises corn syrup. The raw material used may be its corresponding modified or unmodified form, although starches from any starch source may be used.

For purposes of the present invention, the starch hydrolysate comprising a DE of not less than about 18 DE is made by a conversion procedure selected from the group consisting of one-step conversion and multi-step conversion, preferably wherein the conversion procedure is selected from the group consisting of acid conversion, enzyme conversion, and mixed-conversion of both acid and enzyme, and most preferably comprises acid conversion and enzyme-enzyme conversion.

The low DE starch hydrolysates and maltodextrins of the present invention, whether in the form of syrups or dry powder, are particularly suitable for use in food and beverage products. The maltodextrins are especially useful in stable, low DE syrups.

The characteristics of the low DE starch hydrolysates and maltodextrins produced in accordance with the present invention make the products of the invention particularly suitable for applications as carriers for coloring agents, flavors, fragrances and essences, and synthetic sweeteners; spray drying adjuncts for coffee extracts and tea extracts; bulking, bodying and dispersing agents in synthetic creams or coffee whiteners; ingredients promoting a moisture retention in bread, pastry and meats; components of dry soup mixes, bakery mixes, frosting mixes, spice mixes and blends, coverage powders, condiments, gravy mixes, sauce mixes and frozen dairy foods; and in fat mimetics. In addition, they are useful in the formulation of tabulating compounds which can be used in food products or pharmaceutical products, anti-caking agents, whipped products, protective coatings, agglomeration aids, low or reduced-in-calorie foods and beverages. Further, the low DE starch hydrolysates and maltodextrins of the present invention are particularly suitable for use with beverage ingredients, food ingredients, animal feed ingredients, pharmaceutical ingredients, nutraceutical ingredients, cosmetic ingredients and industrial ingredients.

The present invention is also directed to a process for producing solid forms comprising the steps of forming an aqueous composition comprising at least one member selected from the group consisting of low DE starch hydrolysate of the present invention, in its non-hydrogenated, or hydrogenated, or derivatized form; drying said aqueous composition to a moisture content of less than about 10% to result in a substantially dry low DE starch hydrolysate composition; and shaping said dry low DE starch hydrolysate composition to result in a solid form.

In one embodiment of the present invention, the process for producing solid forms may comprise a step of granulating the substantially dry low DE starch hydrolysate composition which may occur during (i.e. as in spray drying) and/or after (i.e. agglomeration or roll compaction) drying to result in a substantially dry granular low DE starch hydrolysate composition. Preferably, the substantially dry granular low DE starch hydrolysate composition may comprise a directly compressible granular powder. The drying step implemented in the present invention may be selected from the group consisting of spray drying, fluidized bed drying, flash-flow technology, rotating dish granulation.

The solid form of the present invention may then comprise a substantially dry low DE starch hydrolysate product of the present invention and/or a substantially dry granular low DE starch hydrolysate product of the present invention.

In a preferred embodiment of the present invention, the aqueous composition comprising the low DE starch hydrolysate of the present invention, in its non-hydrogenated or hydrogenated or derivatized form, as described herein, may further comprise an effective concentration of at least one other ingredient to result in a multi-ingredient solid form.

For purpose of the present invention, the ingredient preferably comprises at least one member selected from the group consisting of food ingredients, animal feed ingredients, beverage ingredients, cosmetic ingredients, pharmaceutical ingredients, nutraceutical ingredients, and industrial ingredients. Other ingredients may be present in the solid form of the present invention like specific substances (e.g. ferrous fumarate, vitamin C) and/or classes of substances (e.g. vitamins, minerals). The ingredient may be in pure form, in combination with other substances, with or without carriers.

The proportion of ingredient to be incorporated in the aqueous composition may be varied depending the strength desired in the final product.

According to the invention, the solid form may be shaped to tablets, caplets, pills, capsules, or lozenges.

Solid forms, manufactured using non-hydrogenated and/or hydrogenated and/or derivatized low DE starch hydrolysate as a substrate to bind an active ingredient and/or fill a solid form matrix, were superior or equal in performance when compared to other starch hydrolysates and polymeric binders/fillers. The solid forms of the present invention are particularly superior to those made using powdered maltodextrins, PVP and HPMC, depending on the active ingredient involved, or analogous binders/fillers previously known or used in the food, pharmaceutical, nutraceutical and chemical industries. The product of the present invention can then easily replace other binders and fillers in formulations, compositions and processes that utilize traditional cellulosics, polymers, gum arabic and maltodextrins.

The low DE starch hydrolysates of the present invention possess equal or superior binding ability and excellent plasticizing functionality, with increased tensile strength, reduced capping pressure and decreased tablet friability compared to cellulosic binders and fillers, polymeric, 18 DE traditional maltodextrins and gum arabic. Inertness and chemical stability of tablet upon aging, compressibility, flowability, plasticity and elasticity are extraordinary characteristics, much sought in universal fillers or binders. These physical, chemical and mechanical characteristics make these new materials economically viable and functionally attractive binder(s) and filler(s) for the nutraceutical, pharmaceutical, chemical and food industry.

In particular, use of the low DE starch hydrolysates of the present invention delivered a wide range of acceptable hardness and substantially non-friable, chemically stable tablets, depending on the active matrix involved. These effects are observed upon agglomeration or granulation of actives with said starch hydrolysates, or even upon just blending actives, with said starch hydrolysates, the whole solid powder mixture being mixed with lubricant and tabletted using one of the conventional processes, like high-speed rotary press or even carver press.

The low DE starch hydrolysates of the present invention also delivered hard, non-friable tablets when produced as agglomerated, directly compressible powder.

Furthermore, the present invention is also directed to a process for producing a coated solid form comprising forming an aqueous with a low DE starch hydrolysate of the present invention and applying to a solid form said aqueous composition in order to form a coated solid form.

More specifically, the process according to the present invention involves a first step consisting forming an aqueous composition comprising at least one member selected from the group consisting of low DE starch hydrolysate having a DE of less than about 25 and a polydispersity index of less than about 5, chemically derivatized low DE starch hydrolysate having a DE less than about 25 and a polydispersity index of less than about 5, and hydrogenated low DE starch hydrolysate having a DE less than about 25 and a polydispersity index of less than about 5. In a preferred embodiment, said aqueous composition further comprises an effective concentration of at least one ingredient selected from the group consisting of sugars, sugar alcohols, cellulosic polymers such as microcrystalline cellulose, hydroxypropylmethyl cellulose, hydroxyethyl cellulose; polymeric ingredients such as polyvinyl pirrolydone (PVP) of varied molecular weight from 20,000 to 2,000,000; starches (modified and/or pregelatinized), protein based material such as gelatine, lecithin and/or pectin, preservatives, flavours, colourings. Mixing can be accomplished by suitable means as are conventionally used for such purpose.

The second step of the process according to the invention comprises applying to a solid form said aqueous composition to form a coated solid form. The solid form to be coated may consist in tablets, caplets, pills capsules, seeds or lozenges, spherules, granules, or particles.

Finally, the present invention is directed to a process for producing a substantially dry granular low DE starch hydrolysate composition comprising the steps of forming an aqueous composition comprising at least one member selected from the group consisting of low DE starch hydrolysate having a DE less than about 25 and a polydispersity index of less than about 5, chemically derivatized low DE starch hydrolysate having a DE less than about 25 and a polydispersity index of less than about 5, and hydrogenated low DE starch hydrolysate having a DE less than about 25 and a polydispersity index of less than about 5; drying said aqueous composition to a moisture content of less than about 10% to result in a substantially dry low DE starch hydrolysate composition; and granulating the low DE starch hydrolysate composition to result in a substantially dry granular low DE starch hydrolysate product.

In a preferred embodiment, said aqueous composition further comprises an effective concentration of at least one other ingredient. Preferably, said other ingredient is selected from the group consisting of food ingredients, animal feed ingredients, beverage ingredients, cosmetic ingredients, pharmaceutical ingredients, nutraceutical ingredients, and industrial ingredients.

In a preferred embodiment of the present invention, said substantially dry granular starch hydrolysate may comprise a directly compressible granular powder.

EXAMPLES

The present invention will now be described in further detail by means of the following representative examples.

Example 1

An acid converted corn syrup having a DE of about 42 and dry solids content of about 23.7% by weight was pumped through a nanofiltration membrane for fractionation using a single pass nanofiltration process. The retentate was recycled to the feed tank until the DE has been reduced to DE 14.5. A thin film composite nanofiltration membrane, ASP 40, made by Advanced Membrane Technology, Inc., San Diego, Calif., is used for test runs. ASP 40 membrane has the following characteristics:

Membrane material: Thin film composite of sulfonated polysulfone on polysulfone,

| | |
|---|---|
| Membrane material: | Thin film composite of sulfonated polysulfone on polysulfone, with a non-woven polyester backing |
| Configuration: | Spiral wound |
| Surface area: | about 5.3 m$^2$ (4 inch diameter and 40 inch length) |
| Operating pressure: | Up to about 600 psi |
| Operating temperature: | Up to about 60° C. |
| Operating pH range: | about 2–11 |
| Maximum chlorine: | about 200 ppm |
| Rejection specification: | NaCl = 30–40%, Lactose = 45–65% |

Preparation of the 42 DE starch hydrolysate starting material was accomplished by conventional acid conversion methods. The conversion process was terminated when the DE value of converted corn starch material reached about 42. The resultant 42 DE, acid converted corn starch material was clarified using a centrifuge to remove residual oil and protein. Following this, a carbon treatment and ion exchange refining process were conducted to de-color and de-ash the material. Finally, the material was evaporated to a dry substance content of about 70% by weight.

Fifteen gallons of acid converted corn syrup having a DE 42 was fed into the feed tank, e.g., as shown in FIG. 1, and diluted to a dry substance content of about 23.7% by weight. The processing line was a single stage system having one nanofiltration membrane element having a 4 inch diameter. The fractionation process was conducted as a batch operation. The permeate was removed from the system, and the retentate was recycled back to the feed tank. The DE value was monitored periodically. Dilution water was periodically added into the feed tank to maintain material dry substance content below about 50% by weight. Retentate recycle was terminated when the DE value of the retentate reached about DE 15. The retentate was then sent forward and collected in a storage container as product. The collected product had collected volume of 13 gallons, and a dry substance content of about 50.5% by weight.

The processing line was operated at a pressure of about 475 psi and a temperature of about 50° C. The permeate flux was 20.3 GFD at the beginning and 1.5 GFD at the end of fractionating. The resultant maltodextrin is substantially free of retrogradation, has a DE of 14.5 and the following carbohydrate profile:

| Component | Weight % D.S. basis |
|---|---|
| Fructose | 0.048 |
| Dextrose | 0.760 |
| DP2 | 1.517 |
| DP3 | 3.557 |
| DP4 | 6.627 |
| DP5 | 8.359 |
| DP6 | 8.442 |
| DP7 | 7.960 |
| DP8 | 7.375 |
| DP9 | 6.759 |
| DP10 | 5.835 |
| DP11–21 | 32.226 |
| DP21+ | 10.534 |

The above-described maltodextrin was further evaporated using a lab rotary vacuum evaporator to obtain low DE starch hydrolysate having different dry solids content. The resultant low DE starch hydrolysate products were evaluated in a designed experiment wherein the variables and their ranges were: dry solids content within the range of about 65% to 75% by weight; storage temperature within the range of about 7° C. to about 49° C.; sorbic acid content within the range of about 0% to about 0.15% by weight; pH within a range of about 2.8 to about 3.5. Color, haze (represented by absorbency at 600 nm) direct count of bacteria, yeasts, and molds were tested at the beginning and after each month of the storage. After 4 months of storage, all 28 tested samples are still clear and retrogradation free.

The polydispersibility index of the resultant maltodextrin is 1.59. The viscosity of the resultant maltodextrin in accordance with the present invention is 65,500 cp at 75.3% dry solids and 7450 cp at 70% dry solids, which is lower than conventionally converted maltodextrin as listed in Table 1 in example 6.

Example 2

In this example, a 36 DE acid converted corn syrup was used as starting material. This starting material was produced by the same process as in Example 1 except that the conversion terminated when the DE value of the acid converted corn syrup material reached about DE 36 and the converted material was not fully ion exchange refined.

The same processing system and nanofiltration membrane as in Example 1 were used to produce the sample in this example. Thirty gallons of 36 DE corn syrup at a dry substance content of about 80% by weight was fed into the feed tank, e.g., as shown in FIG. 1, and diluted to a dry substance content of about 32.6% by weight. The fractionation process was conducted as a batch operation. The permeate was taken out of the processing system, and retentate was recycled back to the feed tank. The DE value was monitored periodically. Dilution water was periodically added into the feed tank to maintain material dry substance content below about 50% by weight. Retentate recycle was terminated when the DE value of the retentate reached about DE 18. The retentate was then sent forward and collected in a storage container as product. The collected product had a collected total volume of about 23 gallons and a dry substance content of about 51.3% by weight.

The operating conditions included a pressure of about 480 psi and a temperature of about 50° C. The permeate flux was 8.2 GFD at the beginning and 1.5 FGD at the end of fractionating. The resultant maltodextrin has a DE of 17.2 and the following carbohydrate profile:

| Component | Weight % D.S. basis |
|---|---|
| Fructose | 0.147 |
| Dextrose | 1.996 |
| DP2 | 3.038 |
| DP3 | 5.803 |
| DP4 | 6.884 |
| DP5 | 9.032 |
| DP6 | 10.626 |
| DP7 | 7.789 |
| DP8 | 5.272 |
| DP9 | 4.218 |
| DP10 | 4.059 |
| DP11–21 | 31.794 |
| DP21+ | 9.342 |

The collected maltodextrin product was further evaporated using a laboratory rotary vacuum evaporator to a dry solids content of 70.2% and 75.5% by weight.

Samples of the maltodextrin product at each of these dry solids contents were stored at room temperature for 2 months and analyzed. Both remained clear and retrogradation free.

The polydispersibility index of the resultant maltodextrin is 2.45. The viscosity of the resultant maltodextrin in accordance with the present invention is 6930 cp at 70% dry solids by weight and at 25° C.

Example 3

An acid converted corn syrup having a D.E. of about 42 and dry solids of 43.5% is pumped through a nanofiltration membrane for fractionation using a single pass nanofiltration pilot plant as shown in the figure. The retentate is recycled to the feed tank until the DE has been reduced to 14.9. The pilot plant used for producing sample products is made by Niro, Inc., Hudson, Wis. A thin film composite polyamide membrane, GH, is used for the test runs and made by Desalination System, Inc., Vista, Calif. GH membrane has the following characteristics:

| | |
|---|---|
| Membrane material: | Thin film composite polyamide |
| Configuration: | Spiral wound |
| Surface area: | About 5.3 m² (4 inch diameter and 40 inch length) |
| Operating pressure: | Up to 600 psi |
| Operating temperature: | Up to 50° C. |
| Operating pH range: | 2–11 |
| Maximum chloride: | 20–50 ppm day |
| Rejection specification: | 50% MgSO4 at 150 psi, and 25 degree C. |

The acid converted 42 DE corn syrup feed material in this example was from corn starch. Corn starch having a dry substance within the range of about 34 to 40% by weight was hydrolyzed using hydrochloric acid at a pH 1.8 and at a temperature of about 128° C. The conversion process was terminated when the DE value of converted corn syrup material reached about 42. The resultant 42 DE, acid converted corn syrup material was clarified using a centrifuge to remove residual oil and protein. Following this, a carbon treatment and ion exchange refining processes were conducted to de-color and de-ash the material. Finally, the material was evaporated to a dry substance content of about 80% by weight.

10 gallons of acid converted corn syrup having a DE 42 was fed into the feed tank, e.g., as shown in FIG. 1, and diluted to a dry substance content of about 43.5% by weight. The process was a single stage system with one nanofiltration membrane element having a 4 inch diameter. The fractionation process was conducted as a batch operation. The permeate was removed from the system, and the retentate was recycled back to the feed tank. Dilution water was periodically added into the feed tank to maintain material dry substance content below about 50% by weight. The retentate recycle was terminated when the DE value of the retentate reached about 15. The collected product had volume of 8 gallons and a dry substance content of about 52.55% by weight.

The process was operated at a pressure of about 485 psi and a temperature of about 50° C. The permeate flux was 8.43 GFD at the beginning and 1.66 GFD at the end of fractionating. The resultant maltodextrin has a DE of 14.9 and the following carbohydrate profile:

| Component | Weight % D.S. |
|---|---|
| Fructose | 0.021 |
| Dextrose | 0.616 |
| DP2 | 1.185 |
| DP3 | 3.649 |
| DP4 | 7.623 |
| DP5 | 10.302 |
| DP6 | 10.011 |
| DP7 | 6.839 |
| DP8 | 7.762 |
| DP9 | 6.679 |
| DP10 | 5.695 |
| DP11–21 | 31.900 |
| DP21+ | 7.719 |

The above maltodextrin was further evaporated using a lab rotary vacuum evaporator to 70% by weight dry solids content for storage stability tests. Two samples, one with no pH adjustment (about pH=4.5) and one with pH adjusted to 3.0 using 7% HCl, were prepared for storage tests. After 4 months storage at room temperature conditions, both samples were still as clear as the original and retrogradation free. There was no microbial growth either.

The polydispersibility index of the resultant maltodextrin is 1.54. The viscosity of the maltodextrin of this example is 7116 cp at 70% dry solids by weight and at room temperature.

Example 4

Starting material for nanofiltration membrane fractionation in this example was a 23 DE enzyme-enzyme converted corn syrup made by, in a first step, liquefying corn starch to 14 DE using bacterial alpha amylase enzyme (Thermamyl T-120, obtained from Novo Nordisk) and, in a second step, saccharifying the resulting liquefied material at a dry solids content of about 30% by weight and at a temperature of about 65° C. using bacterial alpha amylase (Thermamyl T-120 enzyme, Novo Nordisk). The conversion process was terminated when the DE value of the converted material reached about 23. The enzyme-enzyme converted corn starch hydrolysate was clarified using an ultrafiltration membrane to remove oil and protein.

The same processing system and nanofiltration membrane as in Example 1 was used to produce the maltodextrin of this example. Twenty gallons of 23 DE corn syrup=at a dry solids content of about 30% by weight was fed into the feed tank, e.g. as shown in FIG. 1. The fractionation process was conducted as a batch operation. The permeate was taken out of the processing system, and retentate was recycled back to the feed tank. The DE value was monitored periodically. Dilution water was added periodically to maintain the dry solids content of the feed tank material at less than about 40% by weight. Retentate recycle was terminated when the DE value of the retentate reached about 17. The retentate was then sent forward. Following this, a carbon treatment and ion exchange refining process were conducted to de-color and de-ash the retentate. The retentate was then collected in a storage container as a product. The collected product had collected volume of 7 gallons, and a dry substance content of about 47% by weight.

The operating conditions included a pressure of about 500 psi and a temperature of about 45° C. The permeate flux was 12.4 GFD at the beginning and 4.6 GFD at the end of the fractionation. The resultant maltodextrin has a DE of 16.7 and the following carbohydrate profile:

| Component | Weight % D.S. |
| --- | --- |
| Fructose | 0.01 |
| Dextrose | 0.08 |
| DP2 | 1.71 |
| DP3 | 7.38 |
| DP4 | 4.33 |
| DP5 | 20.9 |
| DP6 | 20.58 |
| DP7 | 1.49 |
| DP8 | 1.49 |
| DP9 | 1.93 |
| DP10 | 2.2 |
| DP11–21 | 13.26 |
| DP21+ | 24.64 |

The collected maltodextrin product was further evaporated using a laboratory rotary vacuum evaporator to a dry solids content of 67% by weight. The maltodextrin product was stored at room temperature for 2.5 months and analyzed. The maltodextrin product remained clear and retrogradation free.

The polydispersibility index of the resultant maltodextrin is 4.3. The viscosity of the resultant maltodextrin in accordance with the present invention is 8330 cp at 25° C. and at 70% by weight dry solids, which is lower than conventionally converted maltodextrin listed in Table 3 in example 6.

Example 5

Thirty gallons of acid converted 42 DE corn syrup were fed into a single stage nanofiltration membrane processing system, e.g., as shown in FIG. 1 (NIRO Hudson, Wis.), with a 4 inch spiral nanomembrane (ASP40 from Advanced Membrane Technology, CA). Thirteen gallons of clear liquid retentate having a DE of 13.5 were obtained. The process was performed at 500 psi and 45° C. The membrane used was made from a polysulfonated polysulfone with about 1000 Dalton molecular weight cut off. During the process, permeate flow was removed from the system and the retentate flow was recycled to the feed tank. The test continued until the retentate DE reached about DE 14. The dry solids content of resultant product was about 50% by weight and was further evaporated to a dry solids content of about 70% by weight using a lab scale rotary vacuum evaporator. The resulted product was analyzed using a Brookfield viscometer and HPLC. The viscosity of the analyzed product is only less than about half of the viscosity of conventionally produced material having a similar DE, and the carbohydrate profile was unique in that it had only 2.2% mono- and di-saccharides and 11.6% by weight oligosaccharides with D.P.>21. The analyzed product at 71% by weight dry substance was stored at room condition and remained clear for more than four (4) months.

Example 6

The advantage of the viscosity of the present invention over conventionally enzyme converted maltodextrins is shown in Table 1. In this example, samples produced in Examples 1, 2, and 3, and 4 are analyzed and compared with Glucidex 19, a conventional maltodextrin commercially available from ROQUETTE FRERES, and Maltrin® M180, a conventional maltodextrin commercially available from Grain Processing Co., as to viscosity.

TABLE 1.

Viscosity (cp) at 25° C. of the maltodextrins

| Product | DE | 65% DS | 70% DS | 75% DS |
| --- | --- | --- | --- | --- |
| The present invention with 42 DE feed (example 1) | 14.5 | 1650 | 7450 | 65500 |
| The present invention with 36 DE feed (example 2) | 17.2 | 1560 | 6930 | 7950 |
| The present invention with 42 DE feed (example 3) | 14.9 | — | 7115 | — |
| The present invention with 23 DE feed (example 4) | 16.7 | — | 8330 | — |
| Conventional maltodextrin (Maltrin ® M180, commercially produced by Grain Processing Co.) | 19.4 | — | 21560 | — |
| Conventional maltodextrin (Glucidex 19, commercially produced by Roquette Freres) | 18.0 | 5240 | 18900 | 345000 |

Although not wishing to be bound by any particular theory, it is believed that the advantage of the viscosity of the present invention over conventional maltodextrins was due to narrow carbohydrate profile distribution.

Example 7

Related to Example 6, the carbohydrate profile of the present invention, exemplified in Examples 1,2,3 and 4 has less DP1 and DP2 as well as less DP21+, compared to the commercial maltodextrins having a similar DE, as shown in Table 2.

Again in this example, samples produced in Examples 1, 2, 3, and 4 are analyzed and compared with Glucidex 19 and Maltrin® M180, as in Example 6, to determine their respective carbohydrate profiles and polydispersity (Mw/Mn) as shown in Table 2.

TABLE 2.

Carbohydrate Profile by HPLC and Polydispersity (Mw/Mn) by GPC

|  | Present invention (example 1) | Present invention (example 2) | Present invention (example 3) | Present invention (example 4) | Glucidex 19 (Roquette Freres) | Maltrin ® M180 (Grain Processing Co.) |
|---|---|---|---|---|---|---|
| DP1 % | 0.808 | 2.120 | 0.64 | 0.09 | 1.81 | 2.21 |
| DP2 % | 1.517 | 3.038 | 1.18 | 1.71 | 5.95 | 7.02 |
| DP3 % | 3.557 | 5.803 | 3.65 | 7.38 | 8.27 | 9.20 |
| DP4 % | 6.627 | 6.884 | 7.62 | 4.33 | 6.78 | 7.57 |
| DP5 % | 8.359 | 9.032 | 10.30 | 20.9 | 7.14 | 7.25 |
| DP6 % | 8.442 | 10.626 | 10.00 | 20.58 | 7.74 | 11.66 |
| DP7 % | 7.960 | 7.789 | 6.80 | 1.49 | 5.80 | 8.49 |
| DP8–21 % | 52.195 | 45.343 | 52.00 | 18.88 | 23.08 | 17.50 |
| DP21+ | 10.534 | 9.434 | 7.70 | 24.64 | 33.44 | 29.10 |
| Mw/Mn | 1.59 | 2.45 | 1.54 | 4.3 | 7.07 | 5.65 |

Example 8

Several compositions were prepared according to the present invention as summarized in the following table LDESH means "Low DE Starch Hydrolysate"

| IDENTIFICATION of the product According to the present invention | GENERAL DESCRIPTION OF PRODUCT AND DERIVATION |
|---|---|
| LSH1 | Liquid non-hydrogenated LDESH having a DE = 17.7 and polydispersity = 1.5 Derived by nanofiltration of 42 DE acid converted corn syrup |
| LSH2 | Liquid non-hydrogenated LDESH having a DE = 13.0 and polydispersity = 2.0 Derived by nanofiltration of 28DE acid-enzyme converted corn syrup |
| LSH3 | Liquid non-hydrogenated LDESH having a DE = 18.7 and polydispersity = 2.0 Derived by nanofiltration of 28DE acid-enzyme converted corn syrup |
| LSH4 | Liquid non-hydrogenated LDESH having a DE = 10.9 and polydispersity = 3.3 Produced by nanofiltration of LDESH having a DE = 19 and polydispersity = 3.2, said LDESH being derived by nanofiltration of 28DE enzyme-enzyme converted corn syrup |
| LHSH1 | Liquid hydrogenated LDESH produced by hydrogenating a feedstock of 3 LDESH batches: 1: DE = 18.7 Polydispersity = 2.8 2: DE = 19.3 Polydispersity = 2.4 3: DE = 18.9 Polydispersity = 2.4 said 3 batches being derived by nanofiltration of 42DE acid converted corn syrup |
| SDSH1 | Spray dried non-hydrogenated LDESH produced by spray drying a LDESH comprised of LDESH batches: 1: DE = 17.7 Polydispersity = 1.5 2: DE = 18.5 Polydispersity = 1.6 3: DE = 18.5 Polydispersity = 1.6 4: DE = 16.9 Polydispersity = 1.5 5: DE = 18.5 Polydispersity = 1.6 said 5 batches being derived by nanofiltration of 42 DE acid converted corn syrup |
| SDSH2 | Spray dried non-hydrogenated LDESH produced by spray drying a LDESH having a DE = 19.0 and polydispersity = 3.2, said LDESH being derived by nanofiltration of 28DE enzyme-enzyme converted corn syrup (the same as LSH4) |
| SDHSH1 | Spray dried hydrogenated LDESH produced by spray drying a hydrogenated feedstock of LDESH batches: 1: DE = 19.3 Polydispersity = 1.5 2: DE = 20.0 Polydispersity = 1.5 said 2 batches being derived by nanofiltration of 42DE acid converted corn syrup |
| SDHSH2 | Spray dried hydrogenated LDESH produced by spray drying the LDESH batch of SDSH2 (DE = 19.0, Polydispersity = 3.2) |

Example 9

In the first step, agglomerating solutions of 10–50% LHSH1, LSH1, SDSH2 and SDHSH2 of example 8 were prepared so that the final viscosity of the solutions was about 10–50 cp at room temperature. 3–5% of cellulosic and polymeric solutions were prepared one day earlier and left overnight for hydration. Since the molecular weight of the latter is decisively higher (50,000–1,000,000) than low DE starch hydrolysates in its both forms, non-hydrogenated and hydrogenated, the viscosity was slightly higher and varied from 10 to 400 cp. The viscosity was measured using spindle 3 at 100 rpm Brookfield viscometer.

In the second step, the agglomerating solution was fed via a peristaltic pump to a binary nozzle of the fluidized bed granulator, Aeromatic Strea-1. The operating conditions and parameters are displayed in Table 1.1000 g of ascorbic acid USP or 1000 g of ferrous fumarate USP were added to the fluid bed chamber. First, fluidization was initiated by switching on the fan of the compressor and particle fluidization was attained by adjusting the knob or air flow rate. Granulation temperature, duration of experiment and atomizing pressure were set at the desired value as established in an earlier phase of the experiment. As soon as steady state was attained, i.e. constant temperature, constant air flow rate, the feed (agglomerating liquid) pump was switched on and a jet of atomized liquid was sprayed on the fluidized powder of vitamin C or ferrous fumarate. Experiments lasted until the agglomerating liquid was entirely consumed. After agglomeration, the experiment was extended for an extra 2–3 minutes to dry the agglomerated active powder.

In third step, the agglomerated active material was subjected to extensive analysis to determine the size distribution of the granulated batch which was carried out by the slight scattering technique, and particles classification by the sieve analysis where a detailed anatomy of batch was obtained. Weight fractions were retained for U.S. Standard sieves of 20, 40, 60, 80, 100, and 140 mesh. Bulk and tapped density of the agglomerated powders were immediately measured after granulation to determine granule growth and compressibility index.

TABLE 1.

| | | SETTING | |
|---|---|---|---|
| | OPERATING PARAMETER | VITAMIN C | FERROUS FUMARATE |
| 1 | Inlet air temp (C) | 60 | 50 |
| 2 | Outlet air temp (C) | ≈35 | ≈25 |
| 3 | Air flow rate (m³/h) | 75–100 | 80–90 |
| 4 | Atomizing pressure (bar) | 1 | 1 |
| 5 | Liquid feed flow rate (g/min) | 13.5–14 | 13.5–14 |
| 6 | Atomizing air flow rate (g/min) | 50 | 50 |
| 7 | Mass ratio (liq/air) | 0.28 | 0.28 |

In the fourth step, the granulated active material was classified in a Ro-Tap and the retained fraction between 50 and 16 mesh was collected for tabletting. This fraction was mixed with 1% magnesium stearate lubricant in a planetary mixer for one minute and the mixture was poured into the hopper of the rotary press. Hardness is a measure of strength of tablets and their ability to retain their physical integrity, expressed in terms of Strong Cobb Units, Newtons, Kilopond etc. An average of 10 or more were measured for their hardness in a Dr. Schleuniger hardness tester and the average of these readings was reported herein.

A measure of the tendency of tablets to crumble and dust is expressed in terms of percent of weight loss as determined by the "Roche" test. This test was carried out by sampling twenty tablets from each batch, de-dusting the tablets and weighing the same. The tablets were then subjected to the friability test in Vankel friabilator according to USP standards, i.e., 20 rpm for 4 minutes. The tablets were allowed roll and fall for 4 minutes, and thereafter were carefully de-dusted and weighed again. The loss of weight was reported as the percentage loss from the original weight.

A measure of controlled release of a tablet, is the ability of the tablet to release its active ingredient or load in a designated area of the human body such as stomach or intestines. In a USP certified instrument, a simulated experiment was conducted on vitamin C and ferrous fumarate tablets in a 6-chamber apparatus where agitation was provided at 100 rpm and at 37C in 900 mL water and 0.1N sulfuric acid solutions respectively.

The performance of the binder(s)/filler(s) LSH 1; LSH2; LSH3 and LHSH1 can be divided into three categories: (1) Powder; (2) Tablet; (3) Processing.

1.1. Powder

The granulated powder of vitamin C and ferrous fumarate showed the following outstanding physical characteristics:

Narrow, well-defined and tight particle size distribution irrespective to the active used;

Two-to-five-folds increase in mean particle size;

Lower or equal bulk density compared to other polymeric and cellulosic binders;

Relatively low compressibility index;

Flowable, dust-free and directly compressible granulated powder.

2.1. Tablet

The final solid state delivery system, i.e., tablet using the above granulated powder with the aforementioned binders, i.e., LSH1, LSH2, LSH3 and LHSH1 non-hydrogenated and hydrogenated starch hydrolysates respectively, showed the following outstanding characteristics: Higher, acceptable tablet hardness of a directly compressible nutraceutical, pharmaceutical, food and chemical compositions. Such tablet was determined to be acceptable at low binder level and low compression.

Lower or equal tablet friability defined as "substantially non-friable". In other words, the percent weight loss of tablets due to tumbling and falling as determined by "Roche Test" is less than about 1% from the original weight and such tablet was made with minimal amount of binder, i.e., 5–10%, and relatively low compression 2000 lbs.

Equal or slightly slower rate of active ingredient release as measured according to USP monographs and standards.

Higher chemical stability of tablets, particularly, with LHSH 1, where no fading, discoloration, reactivity with active was found over a period of 8 months compared to cellulosics, traditional starch hydrolysates, gum arabic or even pregelatinized starches.

Substantially better taste, odorless, non-irritating, non-laxative tablets compared to tablets made with cellulosic binders/fillers.

Extremely, shiny, polished surfaces and aesthetically fine tablet compared to tablets made with other polymeric and cellulosics materials.

3.1 Processing

The other nonetheless important parameter is the processing and handling of aforementioned binder(s) and filler(s):

Operational cost savings on heating, mixing and metering the powder of polymeric cellulosic to prepare the aqueous agglomerating liquid.

Three-to-fifteen-fold lower viscosity of agglomerating liquid;

Elimination of anti-foaming agents from use, hydration time etc.

Energy savings and easy liquid handling, due to relatively low viscosity of LSH1, LSH3, LSH2 and LHSH1 compared to aqueous solutions made with the cellulosics, gum arabic, polymeric and starches, which results in lower pressure drop.

Cost effectiveness in other formulations where more expensive ingredients such as HPMC, PVP, gum arabic can be partially or entirely replaced.

Five-to-ten-fold higher dry solid level of infeed;

Shorter granulation time;

TABLE 2

CLASSIFICATION OF LDESH PRODUCTS ACCORDING TO THEIR FUNCTIONALITY

|  | LHSH1 Binder | Filler | LSH1 Binder | Filler | LSH2 Binder | Filler | LSH3 Binder | Filler |
|---|---|---|---|---|---|---|---|---|
| VITAMIN C | +++ | +++ | – | +++ | – | +++ | – | +++ |
| FERROUS FUMARATE | +++ | +++ | ++ | +++ | ++ | +++ | ++ | +++ |

Excellent = +++
Good = ++
Fair = +/–
Poor = –

The aqueous agglomerating liquid of the non-hydrogenated and, in particular, hydrogenated low DE starch hydrolysates described above and represented by LSH1, LSH2, LSH3 and LHSH1 represent a unique composition and carbohydrate profile. The non-hydrogenated liquid maltodextrin LSH1, LSH3 and LSH2 showed an equal or superior performance than conventional maltodextrin 18 DE. However, LHSH1 showed an outstanding performance compared to all LDESH products, conventional maltodextrin 18 DE and the polymeric povidone PVP K30, and cellulosics HPMC E5 and MC-A15 LV. LHSH1 is capable of delivering a solid dosage system at low binder level and relatively low compression. High degree of plastic deformation and low elastic modulus exhibited by the product are two important characteristics delivered in one product. Film forming, cohesiveness and adhesiveness are additional traits that binder should possess which are clearly exhibited by LHSH1. Although conventional maltodextrins are more often used as binders and fillers and the number of patents is large, the performance of LSH1, LSH2, LSH3 and particularly LHSH1 is outstanding and can be easily singled out for its uniqueness and universality.

EXAMPLE 10

The film coating potential using LSH1, LHSH1, SDSH2 and SDHSH2 (SDSH2 and SDHSH2 are the powder form of LSH1 and LHSH1 respectively), conventional 18 DE maltodextrin, and HPMC E5 (Dow Chemical) were investigated using two approaches:

1. Cast a film from a solution containing the film substrate on a slide of glass;
2. Apply a film to coat a discrete particles such as tablets, agricultural seeds and the like to demonstrate the feasibility of the products mentioned above in film coating technology.

Procedure:

The procedure relied on dissolving appropriate amount of SDSH2 or SDHSH2 (approx. from 10 to 70% of solid powder in water) or diluting the liquid product LHSH1 or LSH1 accordingly and then warm the solution for a short period of time and then cast the film. The film was subjected to Scanning Electron Microscopy and optical classical microscopy analysis. The results are summarized in Table 1.

TABLE 1.

Results of film physical appearance casted on a thin glass.

| ITEM | BRITTLENESS AND CRACKINESS | COLOR | MORPHOLOGY OF FILM | REMARKS |
|---|---|---|---|---|
| SDHSH2 | Brittle film with no cracks, only after 6–8 days. | Transparent | • Glassy, nonporous film.<br>• Moderate plasticity;<br>• STRONG adhesive property.<br>• Strong Tackiness and cohesiveness.<br>• Glossy film | It dries up very slowly. It holds on to moisture, when it is left to dry at room temperature. |
| SDSH2 | Brittle film and cracky. Cracks can be seen immediately upon drying. | Transparent | • Glassy, amorphous, nonporous morphology<br>• No plasticity<br>• Moderate adhesiveness<br>• Tackiness<br>• Glossy | The film dries up faster than Lab 9101 with clear microscopic cracks. |
| M 180 | Brittle film. Cracks are evident immediately upon drying. | Transparent | • Glassy film. Nonporous morphology with intense crackiness.<br>• No plasticity<br>• Moderate adhesiveness<br>• Tackiness<br>• Glossy | It dries up like LMD with immediate cracks due contraction of film caused by internal stresses. |
| LSH4 | Brittle film. Cracks appeared upon drying. | Transparent | • Glassy film with nonporous morphology. | Good film capabilities. It dries up like other LMD products with |

TABLE 1.-continued

Results of film physical appearance casted on a thin glass.

| ITEM | BRITTLENESS AND CRACKINESS | COLOR | MORPHOLOGY OF FILM | REMARKS |
|---|---|---|---|---|
| | | | • No plasticity<br>• Adhesiveness<br>• Tackiness<br>• Glossy | evident cracks. |
| HPMC E5 | Continuous plastic film with no cracks. | Unclear blurred, amberlike film | • Plastic property film nonporous morphology<br>• High plasticity<br>• Less-to-no adhesiveness<br>• Minor tackiness<br>• Opaque | • Good film property<br>• It dries very quickly;<br>• It does not hold on to moisture;<br>• Plastic film behavior, no breaking upon bending. |

Film Coating of Tablets and Agricultural Seeds in Wurster Bed.

The process of film coating relied on applying a coat on a discrete particle, e.g., tablet, pill, agricultural seed, particles of nutraceutical nature such as ferrous fumarate, bitter vitamins from the group of vitamin B etc. The process was carried out in a Wurster bed of the UniGlatt, a laboratory scale unit. The process relied on tablets fluidization and upspray the coating substrate containing other ingredients onto the tablets, seeds, particles etc. The operating conditions are summarized in Table 3.

TABLE 2.

Operating Conditions for the Wurster Bed

| | | CORE | |
|---|---|---|---|
| | OPERATING PARAMETER | TABLETS | SEEDS |
| 1 | Inlet air temp (C) | 55–60 | 55–65 |
| 2 | Outlet air temp (C) | 35–45 | 40–50 |
| 3 | Air flow rate (m³/h) | 75–100 | 75–100 |
| 4 | Atomizing pressure (bar) | 1–2 | 1–2 |
| 5 | Liquid feed flow rate (g/min) | 5–8 | 5–8 |
| 6 | Atomizing air flow rate (g/min) | 50 | 50 |

Procedure

300–500 g of tablets or seeds was poured into the Wurster bed chamber which was preheated to 50C before seeds or tablets or powder were added. A solution of the coating material, e.g., SDHSH2 or LHSH1 or LSH4 as the primary film substrate is used within the range of 50 to 90% by weight of the total coating mixture, and most preferably, from 68 to 86% by weight of the coating mixture. In addition to the primary film former or substrate, a secondary film former (optional) can be added to impart extra strength and plasticity to the HSH or SDHSH2 or LHSH1. Suitable secondary film formers are propylene glycol alginate sodium alginate within the range from 2% to 20% by weight of the coating mixture. 5–10% being the most preferred. Depending on the use and application, a plasticizer should be added to improve film performance and add additional plasticity and to eliminate the crackiness of the film. Among the plasticizers used are sorbitol, lycasin (hydrogenated glucose polymer), polyhydric alcohol such as glycerine, polyethylene glycol 300, 400 etc.

By virtue of their molecular stricture, LHSH1 and SDHSH2 as well as conventional maltodextrins exhibit adhesive and cohesive properties, and particularly, SDSH2 and SDSH2. Therefore, to minimize this impact detackifiers such as high molecular weight polymer from the group of polyethylene glycol, for example, PEG 3350 and 8000 can be added. The detackifiers are used from 5% to 25% and most preferred about 12%.

Equally, an additional element is used, however, it is optional in film coating, namely, pigments and Lakes. Certain approved soluble dyes can be used for this purpose, for example, FD & C. yellow #5. An opacifier can be incorporated for the same matter, such an opacifier is titanium oxide or dioxide.

The mixture described above can be used to obtain the final coating solution formula. The dry formula proposed earlier can be diluted to achieve the best results in film coating. For example, 15–25 g of the mixture is added to 75–85 g of water. This DS level solution is used as the coating solution to obtain best results. Depending on the mass increase of tablets, seeds, particle etc. the experimentalist will be able to estimate the amount of coating material needed to achieve about 3 to 5% mass increase or 10 to 20% by weight for tablets and particles respectively. As an example of such formula see Table 3.

TABLE 3.

Experimental formula for tablets, seeds and particles coating

| | COMPONENT | COMP. (%) | REMARKS |
|---|---|---|---|
| 1 | SDSH2; OR SDHSH2; OR HPMC E5; OR LSH4 | 68–86.0 | Film former |
| 2 | Polyethylene glycol/300/400 Sorbitol or/and Lycasin or/and Glycerin or/and | 5.0–10.0 | Plasticizer |
| 3 | Polyethylene glycol 3350 PEG 8000 OR Clear gum C001 | 5.0–25.0 | Detackifier |
| 4 | Propylene glycol alginate or Sodium alginate | 2.0–20. | Secondary film former |
| 5 | Titanium dioxide | 5.0–8.0 | Opacifier |
| 6 | FD &C yellow #5 aluminum lake | 1.5–3.0 | Dye/yellow color |

The experimental run began with switching on the feed pump to introduce the liquid coating material to the nozzle, upon which it is atomized into very small droplets to coat the fluidized particles or tablets. In this respect, it is recommended to optimize the operating conditions for each system to be coated before a final decision is made on whether a need for such amount of plasticizer, detackifier etc. is required.

After the coating solution has been exhausted, an extra 5–10 minutes of drying the cores is necessary to achieve a better results. Obviously, this can impact the integrity of the film and undermine its continuity. The experimentalist will be able to adjust the drying time for each system. The dried material (coated tablets, caplets, seeds) is then spread over a metallic tray for cooling.

- Among the positive aspects of films made with SDHSH2, are that they are clear and transparent and such films are sought by the nutraceutical and pharmaceutical industry.
- SDHSH2 films are harder films and they tend to show high tensile strength compared to HPMC films
- SDHSH2 films are not opaque and characterizes high gloss;
- In the case of SDHSH2 or LHSH1, an additional advantage is the plasticizing effect imposed by the chemical structure of the molecule itself. Therefore, no additional plasticizer may be needed.
- Most of the aqueous dyes, Lakes are soluble in LHSH1 or SDHSH2 solutions and pigments are dispersible too.
- SDHSH2, LHSH1, and LSH4 are compatible with cellulosic and other polymers such as polyvinyl pirrolydone, which introduces an extra dimension to formulate coating material suitable in controlled release coating formulation and the like.

In the claims, means-plus-function clauses are intended to cover the structures described herein as performing the recited function and not only structural equivalents but also equivalent structures.

What is claimed is:

1. A process for producing solid forms comprising the steps of:
   (1) forming an aqueous composition comprising at least one member selected from the group consisting of low DE starch hydrolysate having a DE less than about 25 and a polydispersity index of less than about 5, chemically derivatized low DE starch hydrolysate having a DE less than about 25 and a polydispersity index of less than about 5, and hydrogenated low DE starch hydrolysate having a DE less than about 25 and a polydispersity index of less than about 5, and
   (2) drying said aqueous composition to a moisture content of less than about 10% to result in a substantially dry low DE starch hydrolysate composition,
   (3) shaping said dry low DE starch hydrolysate composition to result in a solid form.

2. The process of claim 1, comprising a step of granulation of the substantially dry low DE starch hydrolysate composition, to result in a granular substantially dry low DE starch hydrolysate composition.

3. The process of claim 1, wherein said drying comprises a member selected from the group consisting of spray drying, fluidized bed drying, flash-flow technology, rotating dish granulation.

4. The process of claim 1, wherein said aqueous composition further comprises an effective concentration of at least one other ingredient.

5. The process of claim 4, wherein said ingredient is selected from the group consisting of food ingredients, animal feed ingredients, beverage ingredients, cosmetic ingredients, pharmaceutical ingredients, nutraceutical ingredients, and industrial ingredients.

6. The process of claim 1, wherein said solid form is shaped to a form selected from the group consisting of tablets, caplets, pills, capsules, and lozenges.

7. The process of claim 2, wherein said substantially dry granular starch hydrolysate composition comprises a directly compressible granular powder.

8. A solid form produced by the process of claim 1.

9. A solid form produced by the process of claim 2.

10. A solid form produced by the process of claim 4.

11. A solid form comprising a substantially dry low DE starch hydrolysate product, wherein said product comprises at least one member selected from the group consisting of low DE starch hydrolysate having a DE of less than about 25 and a polydispersity index of less than about 5, chemically derivatized low DE starch hydrolysate having a DE less than about 25 and a polydispersity index of less than about 5, and hydrogenated low DE starch hydrolysate having a DE less than about 25 and a polydispersity index of less than about 5.

12. A solid form comprising a substantially dry granular low DE starch hydrolysate product, wherein said product comprises at least one member selected from the group consisting of low DE starch hydrolysate having a DE of less than about 25 and a polydispersity index of less than about 5, chemically derivatized low DE starch hydrolysate having a DE less than about 25 and a polydispersity index of less than about 5, and hydrogenated low DE starch hydrolysate having a DE less than about 25 and a polydispersity index of less than about 5.

13. The solid form of claim 11, wherein said solid form further comprises at least one ingredient.

14. The solid form of claim 12, wherein said solid form further comprises at least one ingredient.

15. A process for producing a coated solid form, comprising the steps of:
   (1) forming an aqueous composition comprising at least one member selected from the group consisting of low DE starch hydrolysate having a DE of less than about 25 and a polydispersity index of less than about 5, chemically derivatized low DE starch hydrolysate having a DE less than about 25 and a polydispersity index of less than about 5, and hydrogenated low DE starch hydrolysate having a DE less than about 25 and a polydispersity index of less than about 5, and
   (2) applying to the solid form said aqueous composition in order to form a coated solid form.

16. The process of claim 15, wherein said solid form is a shaped form selected from the group consisting of tablets, caplets, pills, capsules, seeds, lozenges, spherules, granules, or particles.

17. The process of claim 15, wherein said aqueous composition further comprises an effective concentration of at least one ingredient selected from the group consisting of sugars, sugar alcohols, microcrystalline cellulose, hydroxypropylmethyl cellulose, hydroxyethyl cellulose, polyvinyl pirrolydone, gelatin, lecithin, preservatives, flavours, colourings.

18. A coated solid form produced by the process of claim 15.

19. A coated solid form produced by the process of claim 17.

20. A coated solid form product, wherein the coating on said product comprises at least one member selected from the group consisting of low DE starch hydrolysate having a DE of less than about 25 and a polydispersity index of less than about 5, chemically derivatized low DE starch hydrolysate having a DE less than about 25 and a polydispersity index of less than about 5 and hydrogenated low DE starch hydrolysate having a DE less than about 25 and a polydispersity index of less than about 5.

21. The product of claim 20, wherein the coating on said product further comprises at least one other ingredient.

22. The product of claim 21, wherein said other ingredient comprises a member selected from the group consisting of sugar, sugar alcohols, microcrystalline cellulose, hydroxypropylmethyl cellulose, hydroxyethyl cellulose, preservatives, flavors, colorings.

23. A process for producing a substantially dry granular low DE starch hydrolysate composition comprising the steps of:

(1) forming an aqueous composition comprising at least one member selected from the group consisting of low DE starch hydrolysate having a DE less than about 25 and a polydispersity index of less than about 5, chemically derivatized low DE starch hydrolysate having a DE less than about 25 and a polydispersity index of less than about 5, and hydrogenated low DE starch hydrolysate having a DE less than about 25 and a polydispersity index of less than about 5, and (2) drying said aqueous composition to a moisture content of less than about 10% to result in a substantially dry low DE starch hydrolysate composition, (3) granulating the low DE starch hydrolysate composition to result in a granular substantially dry low DE starch hydrolysate product.

24. The process of claim 23, wherein said drying comprises a member selected form the group consisting of spray drying, fluidized bed drying, flash flow technology, rotating dish granulation.

25. The process of claim 23, wherein said substantially dry granular starch hydrolysate composition comprises a directly compressible granular powder.

26. The process of claim 23, wherein said aqueous composition further comprises an effective concentration of at least one other ingredient.

27. The process of claim 23, wherein said ingredient is selected from the group consisting of food ingredients, animal feed ingredients, beverage ingredients, cosmetic ingredients, pharmaceutical ingredients, nutraceutical ingredients, and industrial ingredients.

28. A substantially dry granular low DE starch hydrolysate composition produced by the process of claim 23.

29. A substantially dry granular low DE starch hydrolysate product, wherein said product comprises at least one member selected from the group consisting of low DE starch hydrolysate having a DE less than about 25 and a polydispersity index of less than about 5, chemically derivatized low DE starch hydrolysate having a DE less than about 25 and a polydispersity index of less than about 5, and hydrogenated low DE starch hydrolysate having a DE less than about 25 and a polydispersity index of less than about 5.

* * * * *